US005948453A

United States Patent [19]

Cerny et al.

[11] Patent Number: 5,948,453
[45] Date of Patent: Sep. 7, 1999

[54] FOOD FLAVORANT PREPARATION VIA BIOCONVERSION OF ELEMENTAL SULPHUR

[75] Inventors: Christoph Cerny, Winterthur; Tuong Huynh-Ba, Pully; Walter Matthey-Doret, Belmont S/Lausanne, all of Switzerland

[73] Assignee: Nestec S.A., Vevey, Switzerland

[21] Appl. No.: 08/756,497

[22] Filed: Nov. 26, 1996

[30] Foreign Application Priority Data

Nov. 28, 1995 [EP] European Pat. Off. .............. 95203265

[51] Int. Cl.$^6$ ...................................................... B32B 3/14
[52] U.S. Cl. .............................. 426/48; 426/60; 426/534; 426/650
[58] Field of Search ................... 426/48, 61, 62, 426/60, 520, 534, 535, 650

[56] References Cited

U.S. PATENT DOCUMENTS

| 3,642,497 | 2/1972 | Gunther ................................. 99/140 R |
| 4,080,367 | 3/1978 | Van Den Ouweland et al. .. 260/347.2 |
| 4,194,017 | 3/1980 | Poiger ...................................... 426/533 |

FOREIGN PATENT DOCUMENTS

0395556A1 of 1990 European Pat. Off. .
0582050A1 of 1994 European Pat. Off. .
836694 of 1960 United Kingdom .

OTHER PUBLICATIONS

Translation of Adachi, et al., Japanese Kokai JP–A–58–5164.

Schütz, et al., "Formation of Hydrogen Sulfide from Elemental Sulphur during Fermentation by Wine Yeast", Am. J. Enol. Vitic, vol. 28, No. 3, 1997, pp. 137–144.

Derwent Abstract XRAM Acc. No. C90–143061, WPI Acc. No. 90–329535/44, Abstract of Cohas, European Patent Application Publication No. 0 395 556.

*Primary Examiner*—Donna C. Wortman
*Assistant Examiner*—Brenda G. Brumback
*Attorney, Agent, or Firm*—Vogt & O'Donnell, LLP

[57] ABSTRACT

A flavorant agent is prepared by incubating a medium of baker's yeast, elemental sulfur and a reducing sugar to obtain a reaction medium from which hydrogen sulfide gas evolves and then the reaction medium is treated with heat to obtain the flavorant agent. A further flavorant agent is obtained by separating the supernatant of the reaction medium from reaction medium residue, and the reaction medium or supernatant may be mixed with a flavor precursor material and heated to obtain a flavorant composition.

28 Claims, No Drawings

FOOD FLAVORANT PREPARATION VIA BIOCONVERSION OF ELEMENTAL SULPHUR

BACKGROUND OF THE INVENTION

The present invention concerns a process for the bioconversion of elemental sulfur into sulfide and a process for preparing a flavoring agent, in particular producing a flavour of the meat type.

Given the central part played by hydrogen sulfide in the generation of flavors of the meat type, there is an interest in finding alternative sources of sulfur generating sulfide. One particularly interesting route consists of microbial fermentation. For example, in Amer. J. Enol. Vitic., 1977, 28(3), 137–144, Schütz et al. describe the presence of hydrogen sulfide responsible for the production of bad odors in vinification residues.

SUMMARY OF THE INVENTION

We have found that certain microorganisms which can be used in food, in particular baker's yeast, *Saccharomyces cerevisae*, has the capacity to form hydrogen sulfide from elemental sulfur by biological fermentation. Such a source is particularly interesting since it is abundant and economical.

The process according to the invention is characterized in that a microorganism which can be used in food, in particular baker's yeast, is incubated with elemental sulfur in the presence of a reducing sugar. In order to prepare a flavoring agent of a toasted cheese type, the incubation reaction medium is heat treated.

The invention also concerns a process for preparing a flavoring agent, characterized in that a culture medium of the micro-organism, in particular baker's yeast, is incubated in the presence of elemental sulfur and a reducing sugar at a temperature where it is active, which produces an evolution of gas, in that incubation continues until gas ceases to be evolved, and in that the reaction medium is subsequently heat treated so as to develop the flavor.

DETAILED DESCRIPTION OF THE INVENTION

In order to put the present process into operation, a mixture is prepared containing the microorganism, for example a cream or an extract of baker's yeast, the pH of which is adjusted for example to 5–9, preferably 6–8, by means of a buffer solution. Elemental sulfur is added and, progressively, a reducing sugar, with stirring, preferably vigorous stirring.

The reducing sugar may be, for example, a monosaccharide and in particular a pentose such as xylose, ribose or arabinose, or preferably a hexose such as glucose or fructose. The latter is preferably added progressively, for example in about 60 to 90 min.

As soon as incubation starts, a gaseous evolution of hydrogen sulfide is produced. The incubation conditions are chosen for optimum activation of the microorganism, for example at a temperature of 25 to 40° C., at a pH of 5 to 9 and for 1 to 7 h, with stirring until gas ceases to be evolved.

After incubation, the reaction medium may be heat treated, preferably under reflux at 100° C. for 20 to 40 min. It is through this treatment that the desired flavor develops in the supernatant which can be separated from reaction medium residue, for example by centrifuging, and then, optionally concentrated and dried, for example by spraying or lyophilization in the presence of a support, for example maltodextrin or cyclodextrin.

The invention also concerns the use of reaction media containing the flavoring agent or its reactive precursor as the raw material for the preparation of the process flavorings, mixed with other materials rich in precursors and/or flavor enhancers.

These other materials may, for example, be a soy sauce, a yeast autolysate, sodium chloride, certain sugars, fats and spices.

In order to prepare such flavorings by reaction, the mixture may be reacted by heating at 80–150° C., preferably at around 100° C. for 30 min to 4 h.

It is then possible to add a support to the reaction product, for example maltodextrin or cyclodextrin, and then to dry the mixture at a moderate temperature, for example at 60–70° C. under vacuum.

Such flavourings may be incorporated in foods intended for human or animal consumption.

EXAMPLES

The following examples illustrate the invention. In these, the percentages and parts are by weight, unless stated to the contrary.

Examples 1–3

Commercial creamed baker's yeast, *Saccharomyces cerevisae* with 22–28% dry matter was clarified by centrifuging and the supernatant was discarded. The residue was then mixed with a 0.1 M aqueous solution of phosphate buffer of the chosen pH.

300 ml of this cream of whole cells was then placed in a glass reactor which was fitted with a temperature probe set to 30° C., a stirrer revolving at 600 rpm and a condenser, and which was attached to a pH-stat maintaining the pH at the chosen value by addition of 2N aqueous solution of sodium hydroxide. To this was added 0.8 g (25 mmol) of elemental colloidal sulfur and then, drop-wise, an autoclaved glucose solution (18 g, 100 mmol, dissolved in 30 ml of water), with the same pH, the latter addition taking 90 min.

As soon as the glucose began to be added a spontaneous evolution of gas was observed which ceased after 5 h of incubation. It was possible to quantify this evolution by means of a trap in the form of a flask mounted at the outlet from the condenser and containing 60 ml of 0.5 M aqueous solution of lead (II) nitrate.

After 6 h of fermentation, the pH of the culture medium was adjusted, if necessary, to 6 and the black precipitate of lead sulfide formed in the trap was then collected and dried in an oven at 100° C. for 12 h. The respective quantities by weight of hydrogen sulfide produced, calculated as lead sulfide, as well as the yields of hydrogen sulfide are shown in Table 1 below.

TABLE 1

| Example, pH | 1, pH 6 | 2, pH 7 | 3, pH 8 |
| --- | --- | --- | --- |
| PbS (mg) | 1420 | 1765 | 2548 |
| PbS (mmol) | 5.94 | 7.38 | 10.7 |
| Hydrogen sulfide yield (%) | 23.8 | 29.5 | 42.6 |

Example 4

After incubation according to Example 1, the culture medium was heated at 100° C. for 30 min. After cooling to room temperature, the supernatant was separated from incubation residue other medium by centrifuging for 15 min at 5000 rpm, the residue was then extracted with water, and the supernatant was once again separated by centrifuging and the two supernatants were combined.

After having adjusted the pH of the supernatant to 4 with a 2N aqueous solution of hydrochloric acid, it was saturated with sodium chloride and the sample was extracted with 300 ml of diethyl ether by means of a liquid-liquid extractor, the organic phase was separated off, dried over sodium sulfate, concentrated in a Vigreux column to a volume of 5 ml, and the concentrated solution obtained was placed in a freezer at −40° C. until analysed.

The concentrated extract was analyzed at the olfactory level as well as chemically.

Analysis by gas chromatography was carried out on a Carlo Erba Mega 2 chromatograph fitted with a cold injector and a flame ionization detector (GC-FID). A flame photometric detector was used (GC-FPD) for the sulfur compounds. The capillary columns were DB-5 and DB-FFAP, 30 m×0.32 mm, film thickness 0.25 micrometres, from J & W Scientific, Folsom, USA. The carrier gas was helium (65 kPa) with an addition of nitrogen (40 kPa) for the GC-FID. Olfactory analysis was carried out with the aid of the technique of gas chromatography coupled to olfactometry (GC/O). For this purpose, the gaseous effluent was divided into two equal portions. Half went to the FID detector and the other half was led to a device where the volatile constituents were sniffed and the nature of their odour described by the analyst. This olfactometric analysis was carried out by two analysts.

The retention indices (RI) were calculated by linear interpolation.

The analyses were confirmed by establishing spectra produced by coupling a gas chromatograph to an electron impact mass spectrograph (GC/EI-MS, HP 5890/HP 5971) under the same operating conditions as for GC-FID.

The results for the main sulfur compounds identified are shown in Table 2 below.

TABLE 2

| Compound | RI (FFAP), FID | RI (FFAP), FPD | RI (FFAP), Sniffing | Odor | FFAP-FPD Area of peaks (%) |
|---|---|---|---|---|---|
| O-methyl thioacetate | — | 1005 | 1002 | Fruity, sweet, buttery | 1.87 |
| S-methyl thioacetate | 1053 | 1060 | 1056 | Fruity | 2.02 |
| S-ethyl thioacetate | 1072 | 1100 | 1085 | Fruity, sweet | 0.18 |
| Thioacetic acid | 1107 | 1130 | 1118 | Acid, meat-like, roasted | 78.38 |
| S-methyl-thio thioacetate | 1464 | 1466 | 1470 | Toasted cereal | 2.33 |
| S-methyl-thiomethyl thioacetate | — | 1535 | 1545 | Meat-like, stock | 1.33 |
| 3-methyl-thio-1-propanol | 1718 | 1722 | 1729 | Vegetable, potato | 2.87 |

—: not measured

Other different sulfur compounds not identified represented 7.9% of the total area of the peaks and contributed to the odor of vegetable stock/cereals.

It was noted that the concentrated extract had overall a strong flavor resembling toasted cheese similar to that of toasted rind produced in a cheese fondue or a raclette.

Example 5

The culture medium produced by incubation according to Example 1 was used in a reaction for producing a meat flavor by heating the ingredients except maltodextrin in the proportions shown in Table 3 below for 150 min at 100° C. and at pH 5. Following the reaction, maltodextrin was added and the mixture was dried at 65° C. under vacuum. As a comparison, the same reaction was carried out with baker's yeast which had not been incubated with sulfur, without added sodium sulfide (comparison 1), with added sodium sulfide (comparison 2) and with cysteine (at the rate of 1 mole of cysteine per ⅕th mole of sulfide produced by incubation) (comparison 3).

TABLE 3

| Ingredients (%) | Example 5 | Comparison 1 | Comparison 2 | Comparison 3 |
|---|---|---|---|---|
| Salt, onion extract, powdered soy sauce | 28.6 | 28.6 | 28.6 | 28 |
| Chicken meat meal, chicken fat | 6.5 | 6.5 | 6.5 | 6.4 |
| Sucrose, xylose, glucose | 6.1 | 6.1 | 6.1 | 6 |
| Yeast extract | 5.5 | 5.5 | 5.4 | 5.4 |
| Creamed yeast incubated with sulfur | 42.5 | — | — | — |
| Creamed yeast incubated without sulfur | — | 42.5 | 42.5 | 42.5 |
| Sodium sulfide (60% crystalline) | — | — | 0.2 | — |
| Cysteine HCl | — | — | — | 1 |
| Maltodextrin | 10.8 | 10.8 | 10.8 | 10.8 |

When a culture medium containing 6 g of flavouring and 1 g of NaCl dissolved in 500 ml of hot water was tasted by a panel of five experienced persons, the extract prepared according to the invention proved to have a distinctly meaty flavor compared to the general note of stock for comparison 1, but however, the comparison 2 had a meaty flavour with a slight accent of sulfur. The flavour of the extract prepared according to the invention was very close to that of comparison 3.

We claim:

1. A process for preparing a flavorant agent composition comprising:
   incubating a medium comprising a baker's yeast culture, elemental sulfur and a reducing sugar to obtain a reaction medium from which hydrogen sulfide gas evolves and which comprises a supernatant and a residue; and subsequently
   heating the reaction medium under reflux to obtain a flavorant composition comprising a heat-treated supernatant and a heat-treated residue.

2. A process according to claim 1 further comprising separating the heat-treated supernatant from the heat-treated residue to obtain a supernatant flavorant composition.

3. A process according to claim 1 or 2 further comprising, while incubating, maintaining the medium at a pH of from 5 to 9.

4. A process according to claim 2 further comprising drying the supernatant flavorant composition.

5. A process according to claim 4 wherein the supernatant flavorant composition is dried under vacuum at a temperature of from 60° C. to 70° C.

6. A process according to claim 2 further comprising drying the supernatant flavorant composition with a support selected from the group consisting of maltodextrin and cyclodextrin.

7. A process according to claim 2 further comprising concentrating the supernatant flavorant composition to obtain a concentrated flavorant composition.

8. A process according to claim 7 further comprising drying the concentrated flavorant composition.

9. A process according to claim 2 wherein the flavorant composition is centrifuged to separate the heat-treated supernatant from the heat-treated residue.

10. A process according to claim 1 further comprising first adding the elemental sulfur to the baker's yeast culture and then adding the reducing sugar to the medium progressively over time while incubating.

11. A process according to claim 10 wherein the reducing sugar is added progressively for a time of from 60 to 90 minutes.

12. A process according to claim 1 wherein the medium is incubated with stirring at a temperature of from 25° C. to 40° C. for from 1 to 7 hours.

13. A process according to claim 12 wherein the medium is incubated with the stirring for a time until evolution of hydrogen sulfide gas ceases.

14. A process according to claim 13 wherein the medium is incubated with the stirring at a pH of from 5 to 9.

15. A process according to claim 1 or 2 wherein the reaction medium is heated under reflux for from 20 to 40 minutes.

16. A process according to claim 1 wherein the baker's yeast is selected from the group consisting of a baker's yeast cream and a baker's yeast extract.

17. A process according to claim 1 wherein the reducing sugar is a monosaccharide selected from the group consisting of a pentose and a hexose sugar.

18. A process according to claim 17 wherein the monosaccharide is selected from the group consisting of xylose, ribose, arabinose, glucose and fructose.

19. A process for preparing a flavoring agent composition comprising:

incubating a medium comprising a baker's yeast culture, elemental sulfur and a reducing sugar to obtain a reaction medium from which hydrogen sulfide gas evolves and which comprises a supernatant and a residue; and combining a flavor precursor material with the reaction medium to obtain a reaction medium and precursor mixture; and heating the mixture at a temperature of from 80° C. to 150° C. to obtain a flavorant composition.

20. A process according to claim 19 further comprising, while incubating, maintaining the medium at a pH of from 5 to 9.

21. A process according to claim 19 further comprising first adding the elemental sulfur to the baker's yeast culture and then adding the reducing sugar to the medium progressively over time while incubating.

22. A process according to claim 21 wherein the reducing sugar is added progressively for a time of from 60 to 90 minutes and further comprising stirring the medium while incubating the medium and incubating until evolution of hydrogen sulfide gas ceases.

23. A process according to claim 19 further comprising drying the flavorant composition with a support selected from the group consisting of maltodextrin and cyclodextrin.

24. A process for preparing a flavoring agent composition comprising:

incubating a medium comprising a baker's yeast culture, elemental sulfur and a reducing sugar to obtain a reaction medium from which hydrogen sulfide gas evolves and which comprises a supernatant and a residue; and separating the reaction medium supernatant from the residue to obtain an isolated supernatant;

combining a flavor precursor material with the isolated supernatant to obtain a supernatant and precursor mixture; and heating the mixture at a temperature of from 80° C. to 150° C. to obtain a flavorant composition.

25. A process according to claim 24 further comprising, while incubating, maintaining the medium at a pH of from 5 to 9.

26. A process according to claim 24 further comprising first adding the elemental sulfur to the baker's yeast culture and then adding the reducing sugar to the medium progressively over time while incubating.

27. A process according to claim 26 wherein the reducing sugar is added progressively for a time of from 60 to 90 minutes and further comprising stirring the medium while incubating until evolution of hydrogen sulfide gas ceases.

28. A process according to claim 24 further comprising drying the flavorant composition with a support selected from the group consisting of maltodextrin and cyclodextrin.

* * * * *